US012797249B2

(12) United States Patent
Albert

(10) Patent No.: US 12,797,249 B2
(45) Date of Patent: Nov. 17, 2026

(54) MYRINGOTOMY TUBE WITH A MULTI-VISUAL DESIGN

(71) Applicant: Children's Hospital Medical Center of Akron, Akron, OH (US)

(72) Inventor: Samuel Albert, Akron, OH (US)

(73) Assignee: Aware Medical LLC, Cincinnati, OH (US)

( * ) Notice: Subject to any disclaimer, the term of this patent is extended or adjusted under 35 U.S.C. 154(b) by 1046 days.

(21) Appl. No.: 17/498,356

(22) Filed: Oct. 11, 2021

(65) Prior Publication Data

US 2022/0110796 A1 Apr. 14, 2022

Related U.S. Application Data

(60) Provisional application No. 63/089,687, filed on Oct. 9, 2020.

(51) Int. Cl.
*A61F 11/20* (2022.01)
*A61B 90/92* (2016.01)

(52) U.S. Cl.
CPC ............ *A61F 11/202* (2022.01); *A61B 90/92* (2016.02)

(58) Field of Classification Search
CPC ............ A61F 11/202; A61F 2250/005; A61M 39/1011; A61B 90/92
See application file for complete search history.

(56) References Cited

U.S. PATENT DOCUMENTS

| | | | | |
|---|---|---|---|---|
| 3,020,912 A * | 2/1962 | Chester | A61B 17/32 408/124 |
| 3,935,640 A * | 2/1976 | Cohan | A61C 3/00 433/150 |
| 4,695,275 A * | 9/1987 | Bruce | A61F 11/202 604/264 |
| 6,613,002 B1 | 9/2003 | Tanisha et al. | |
| 9,205,213 B2 | 12/2015 | Mythen | |
| 10,369,047 B2 | 8/2019 | Peartree et al. | |
| 10,806,618 B2 | 10/2020 | Dillon et al. | |
| 2003/0018291 A1* | 1/2003 | Hill | A61F 11/202 604/8 |

(Continued)

FOREIGN PATENT DOCUMENTS

| | | |
|---|---|---|
| CN | 102700054 A | 10/2012 |
| CN | 101305930 B | 2/2013 |

(Continued)

OTHER PUBLICATIONS

The International Search Report and The International Written Opinion of the International Searching Authority, or the Declaration of corresponding PCT Application No. PCT/US2021/054388, dated Jan. 10, 2022, 15 pages.

*Primary Examiner* — Leslie R Deak
(74) *Attorney, Agent, or Firm* — Tucker Ellis LLP

(57) ABSTRACT

One or more techniques and/or systems are disclosed for a myringotomy tube including a tube body having a first end and a second end. The tube body may comprise a shaft operably connecting the first end and the second end. The first end may comprise a first visual element. The second end may comprise a second visual element. The first visual element may be different than the second visual element. The myringotomy tube may be a single piece. The myringotomy tube may be multiple pieces.

18 Claims, 9 Drawing Sheets

(56) References Cited

U.S. PATENT DOCUMENTS

| | | | | |
|---|---|---|---|---|
| 2005/0175703 | A1* | 8/2005 | Hunter | A61L 31/16 514/453 |
| 2011/0112546 | A1 | 5/2011 | Jaun, Jr. et al. | |
| 2020/0281772 | A1* | 9/2020 | Loushin | A61F 11/202 |
| 2022/0370253 | A1* | 11/2022 | Vaughan | A61F 2/958 |

FOREIGN PATENT DOCUMENTS

| | | | |
|---|---|---|---|
| JP | 2020-503928 | A | 2/2020 |
| WO | 2005/042079 | A1 | 5/2005 |
| WO | 2015168642 | A1 | 11/2015 |
| WO | 2019086608 | A1 | 5/2019 |

* cited by examiner

MYRINGOTOMY TUBE WITH A MULTI-VISUAL DESIGN

This nonprovisional patent application claims priority to provisional application having application No. 63/089,687 filed on Oct. 9, 2020, the entirety of which is incorporated by reference.

BACKGROUND

Myringotomy tube placement is a surgical procedure of the eardrum or tympanic membrane. A small incision is made through the ear canal into the tympanic membrane. A myringotomy tube is placed into the tympanic membrane. Part of the tube rests in the middle ear space and part rests in the ear canal. The ear canal is a narrow, tortuous, tubular structure, which can make placement of the tube difficult at times. The myringotomy tubes may remain in the eardrum for 6 to 18 months on average. Then the tubes extrude into the ear canal. If the myringotomy tubes do not extrude on their own and remain in the tympanic membrane for a prolonged period of time, a perforation of the tympanic membrane may develop. Again, because the ear canal is narrow and tortuous, it is often difficult for the practitioners to determine if a myringotomy tube has extruded or is still in place in the tympanic membrane. Therefore, what is needed is a myringotomy tube that helps overcome the above mentioned problems.

SUMMARY

This Summary is provided to introduce a selection of concepts in a simplified form that are further described below in the Detailed Description. This Summary is not intended to identify key factors or essential features of the claimed subject matter, nor is it intended to be used to limit the scope of the claimed subject matter.

In one implementation, there is provided an ear tube that may comprise a tube body comprising a first end and a second end. The tube body may comprise a shaft operably connecting the first end and the second end; wherein the first end may comprise a first visual element. The first visual element. The second end may comprise a second visual element, the second visual element. The first visual element may be different then the second visual element.

In another example implementation, there is provided a method for forming an ear tube from multiple pieces. The method may comprise the step of forming a first portion comprising a first visual element through a molding process, wherein the first visual element may comprise a first color or pattern. The first portion may comprise a first end, including a first flange, and a shaft connected to the first flange. Molding a second portion may comprise a second visual element over the first portion. The second portion may be fused or otherwise connected to the second portion. The second portion comprising a second flange, wherein the second portion may be retained on the first portion through a locking mechanism. The method may further comprise the step of creating a visually distinguishable line of demarcation between the first visual element and the second visual element. The first visual element may comprises a first color or pattern and the second visual element may comprise a second color or pattern. The first visual element may be different than the second visual element.

In another implementation, a method may be provided for forming an ear tube from a single unitary piece. The method may comprise the step of injecting silicone material at one time in precise quantities into a mold. The silicone material may be injected from two different locations that are disposed laterally relative to the mold to fabricate the ear tube. The injected material may comprise a first visual element and a second visual element. The first visual element may comprise a first color or pattern. The second visual element may comprise a second color or pattern different than the first color or pattern. The method may further comprise the step of forming an ear tube body from the silicone material. The tube body may comprise a first end, a second end, and a shaft operably connecting the first end and the second end. The ear tube body may comprise a line of demarcation between the first visual element and the second visual element provided by the first color or pattern being visually distinguishable from the second color or pattern To the accomplishment of the foregoing and related ends, the following description and annexed drawings set forth certain illustrative aspects and implementations. These are indicative of but a few of the various ways in which one or more aspects may be employed. Other aspects, advantages and novel features of the disclosure will become apparent from the following detailed description when considered in conjunction with the annexed drawings.

BRIEF DESCRIPTION OF THE DRAWINGS

What is disclosed herein may take physical form in certain parts and arrangement of parts, and will be described in detail in this specification and illustrated in the accompanying drawings which form a part hereof and wherein.

DETAILED DESCRIPTION

Figure 1A:
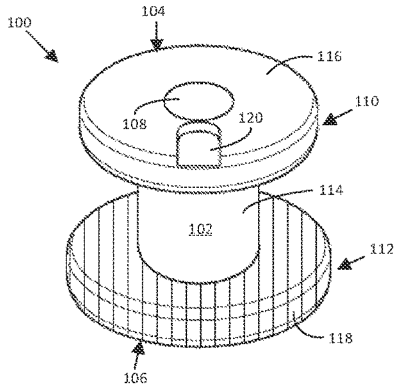
FIGS. 1A-1C are perspective views illustrating a first example implementation of a myringotomy tube in accordance with this disclosure.
Figure 1B:
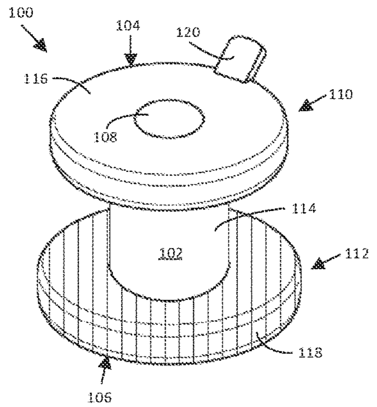
Figure 1C:
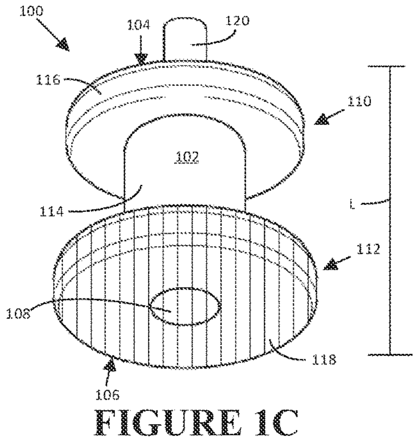
Figure 2:
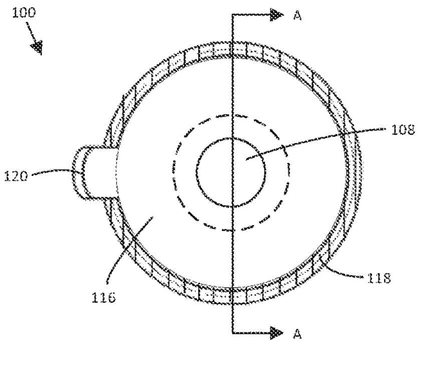
FIG. 2 is a top view of the first example implementation of the myringotomy tube shown in FIGS. 1A-1C.
Figure 3:
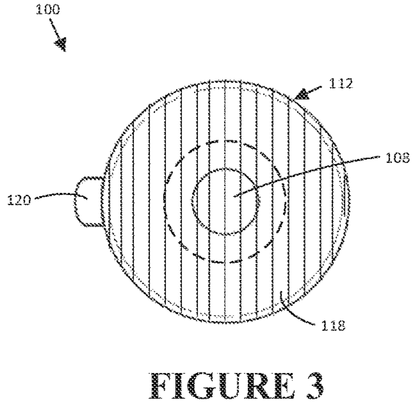
FIG. 3 is a bottom view of the first example implementation of the myringotomy tube shown in FIGS. 1A-1C.
Figure 4:
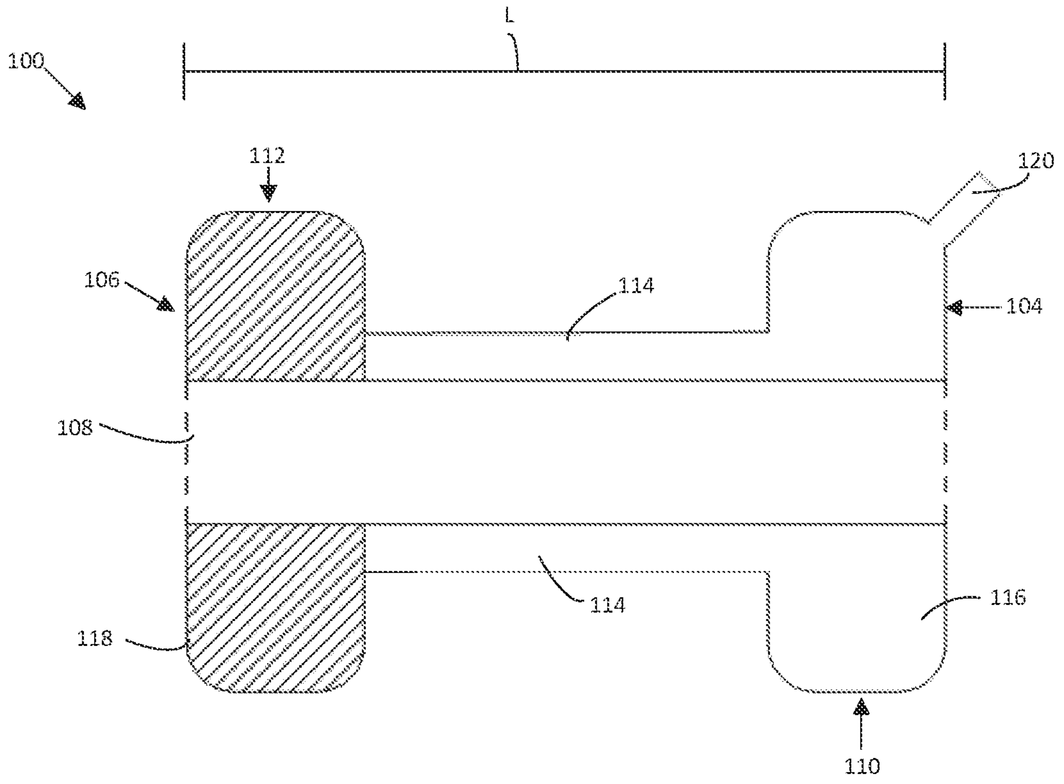
FIG. 4 is a cross sectional view of the first example implementation of the myringotomy tube shown in FIG. 2 taken along line A-A.
Figure 5A:
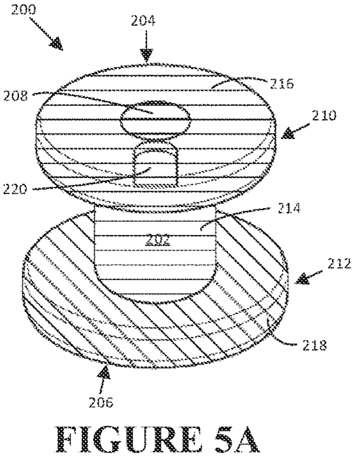
FIGS. 5A-5C are perspective views illustrating a second example implementation of a myringotomy tube in accordance with this disclosure.
Figure 5B:
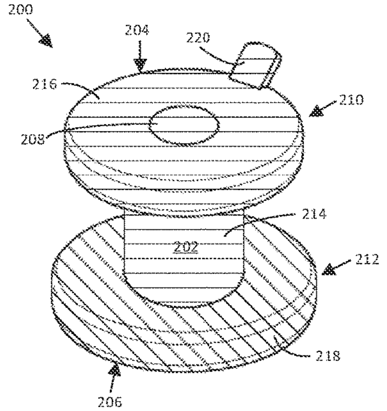
Figure 5C:
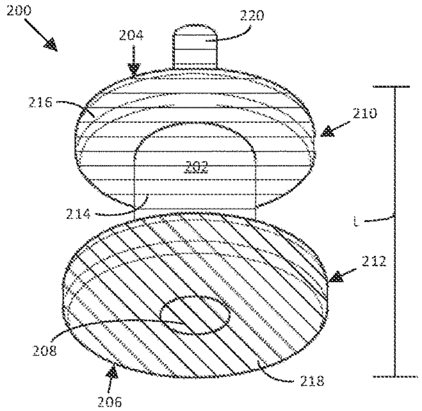
Figure 6:
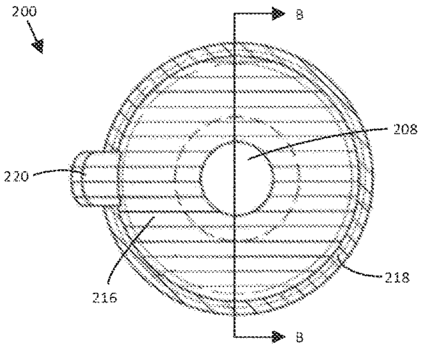
FIG. 6 is a top view of the second example implementation of the myringotomy tube shown in FIGS. 5A-5C.
Figure 7:
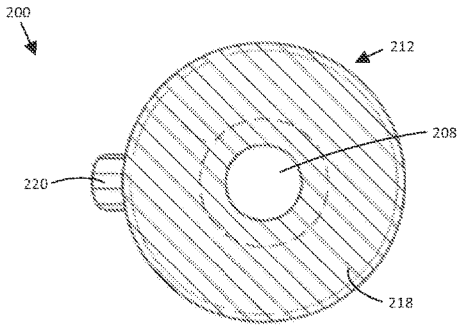
FIG. 7 is a bottom view of the second example implementation of the myringotomy tube shown in FIGS. 5A-5C.
Figure 8:
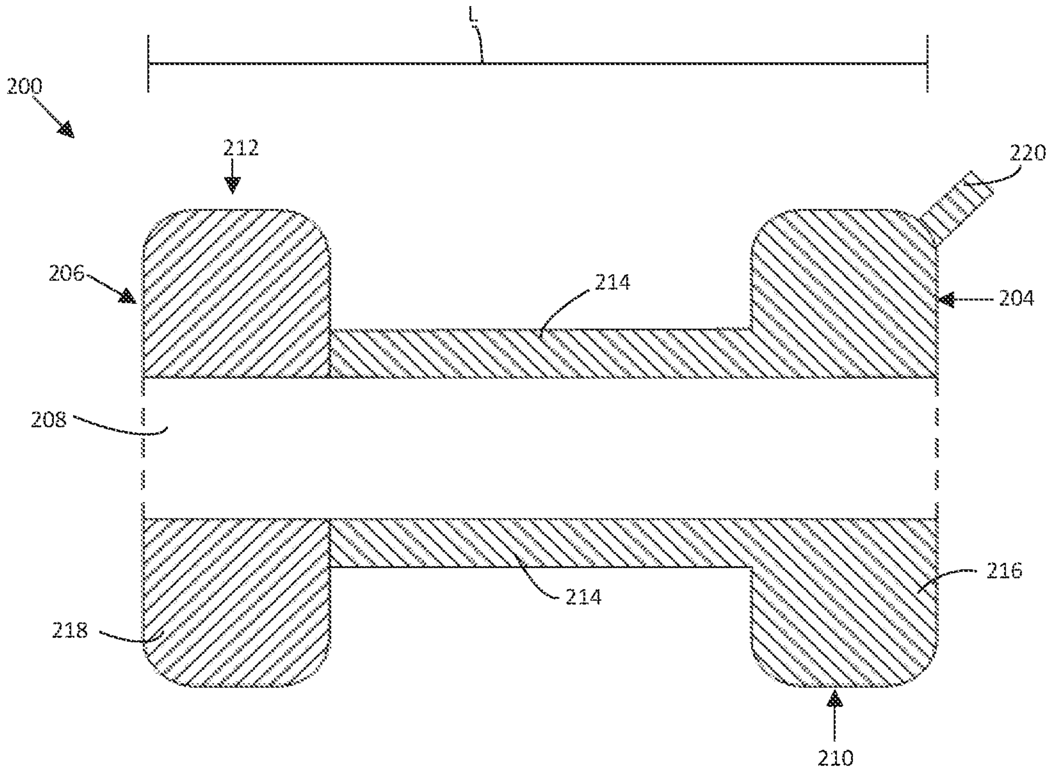
FIG. 8 is a cross sectional view of the second example implementation of the myringotomy tube shown in FIG. 6 taken along line B-B.

The claimed subject matter is now described with reference to the drawings, wherein like reference numerals are generally used to refer to like elements throughout. In the following description, for purposes of explanation, numerous specific details are set forth in order to provide a thorough understanding of the claimed subject matter. It may be evident, however, that the claimed subject matter may be practiced without these specific details. In other instances, structures and devices are shown in block diagram form in order to facilitate describing the claimed subject matter.

Various embodiments and aspects will be described with reference to details discussed below, and the accompanying drawings will illustrate the various embodiments. The following description and drawings are illustrative and are not to be construed as limiting. Specific details are described to provide a thorough understanding of various embodiments. In certain instances, well known or conventional details are not described.

Ear tubes may be myringotomy tubes, ventilation tubes, or tympanostomy tubes. As used herein, the disclosure herein may apply to any form of ear tube, including myringotomy tubes, ventilation tubes, or tympanostomy tubes.

Figure 13:
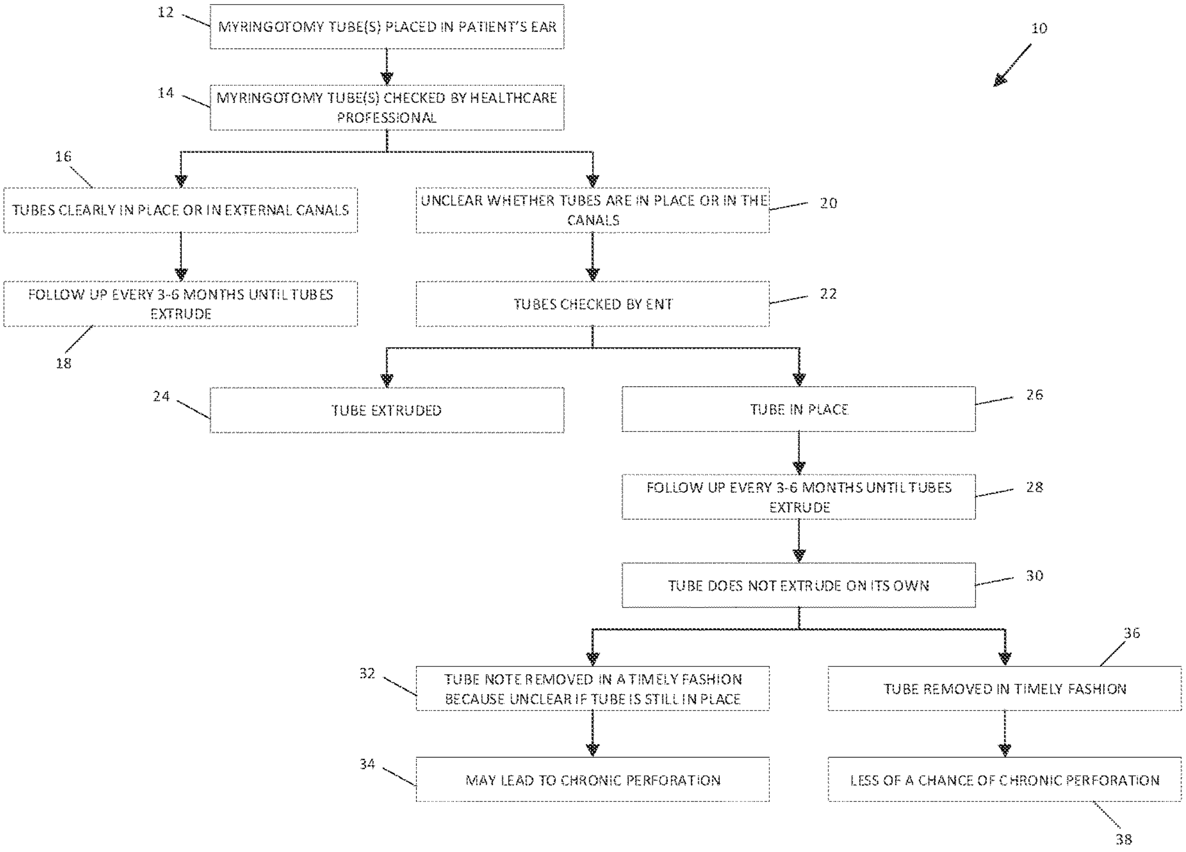
FIG. 13 is a flow diagram providing an example implementation of using conventional myringotomy tubes.

FIG. 13 is a flow diagram showing an example implementation 10 of using myringotomy tubes, otherwise known as ear tubes. At reference numeral 12 the myringotomy tubes are placed in a patient's ears by a medical professional to treat recurrent or chronic otitis media. At reference numeral 14, the myringotomy tubes are checked by a healthcare professional such as, for example, a pediatrician, internists, family practice, nurse practitioner, etc. At reference numeral 16, the ear tubes are determined to be clear in place or clearly in external canals of the patient. At 18, upon this determination, there is a follow-up appointment scheduled every three to six months until the ear tubes extrude. At reference numeral 20, it is unclear whether the tubes are in place or in the canals of the patient. At 22, there is a referral to an ear, nose and throat ("ENT") specialist to check the tubes. At reference numeral 24, the ENT determines the tubes are extruded. At reference numeral 26, the ENT determines the tube is in place. At reference numeral 28, upon this determination, there is a follow-up appointment scheduled every three to six months until the ear tubes extrude. At reference numeral 30, the ear tube does not extrude on its own. At reference numeral 32, an ear tube is not removed in a timely fashion because it was difficult to determine if the ear tube was still in place in the patient's ear. At reference numeral 34, this scenario may lead to chronic perforation. At reference numeral 36, the tube is removed in a timely fashion. At reference numeral 38, there is less of a chance of chronic perforation as a result of removing the tube in a timely fashion.

Referring now to FIGS. 1-4, a first example implementation of an ear tube 100 is shown, which may be also be referred to as a myringotomy tube. The ear tube 100 may comprise a tube body 102 comprising a first end 104 and a second end 106. The tube body 102 may have a lumen 108 formed therethrough to facilitate drainage of fluid from the middle ear (not shown). In some implementations, the lumen 108 may be centrally located about an axis extending from the first end 104 to the second end 06. The ear tube 100 may comprise a length L defined as the distance between the first end 104 and the second end 106. The length L of the ear tube 100 may be generally less than 2 mm, which is smaller than a match head, because the ear tube 100 may be generally intended for pediatric use in children between 1 to 3 years of age. As an example, in some implementations the ear tube 100 has a length L of approximately 1.5 mm.

In this implementation, the ear tube 100 may at least one visual element. The at least one visual element can comprise a color, pattern, texture, and/or composition that serves as a visual indicator to assist placement of the ear tube 100 in a patient and to improve monitoring of the ear tube 100 in a patient's ear. In one non-limiting example implementation, the ear tube 100 may comprise a first end 104 including a first visual element 110 such as, for example, a first color and/or pattern and a second end 106 including a second visual element 112 such as, for example, a second color and/or pattern that is visually distinguishable from the first visual element 110. The first visual element 110 may be different than the second visual element 112. In another non-limiting example implementation, the first visual element 110 of the first end 104 may extend a certain length of the ear tube 100 such that the surgeon positioning the ear tube 100 into the patient or observing an already placed ear tube is provided with a visual indication whether the ear tube 100 is in place.

In some implementations, the tube body 102 may comprise a shaft 114 operably connecting a first flange 116 and a second flange 118. A tab 120 may be operably connected to the first flange 116. The first flange 116, shaft 114, and second flange 118 may be interconnected by a lumen 108 that extends through each of the first flange 116, the shaft 114, and the second flange 118 between the first end 104 and the second end 106. In one implementation, the first flange 116 may have a smaller diameter than the second flange 118. In another implementation, the first flange 116 and the shaft 114 may together comprise the first visual element 110, such as a first color or pattern. The second flange 118 may comprise the second visual element 112, such as a second color or pattern that is different than the first color or pattern. In another implementation, the ear tube 100 may comprise a third visual element, for example, a color band that is visually distinguishable from the first and second visual elements 110 and 112 disposed on the ear tube body 102.

Table 1 below provides a non-exhaustive list of potential color combinations for implementations comprising a multicolored ear tube 100, or multicolored myringotomy tube, in which the color of the first visual element 110 is visually distinguishable from the color of the second visual element 112. In other implementations, the first visual element 110 comprises a pattern that is visually distinguishable from the pattern of the second visual element 112. In yet other implementations, the first visual element 110 comprises a combination of color and pattern that is visually distinguishable from the color and pattern combination of the second visual element 112.

Color combinations include, but are not limited to the following, together with all shades and combination of colors:

TABLE 1

| Visual Element | Visual Element |
|---|---|
| Blue | Green |
| Blue | Yellow |
| Blue | Red |

TABLE 1-continued

| Visual Element | Visual Element |
|---|---|
| Blue | Violet |
| White | Black |
| White | Blue |
| White | Green |
| White | Red |
| White | Yellow |
| White | Violet |
| Black | Blue |
| Black | Green |
| Black | Red |
| Black | Violet |
| Black | Yellow |
| Green | Red |
| Green | Yellow |
| Green | Violet |
| Yellow | Red |
| Yellow | Violet |

Referring now to FIGS. 5-8, a second example implementation of an ear tube 200 is shown, which may be also be referred to as a myringotomy tube. This implementation of an ear tube 200 has a similar structure to the ear tube 100 illustrated in FIGS. 1-4. For the sake of brevity, identical features will mostly not be discussed.

In FIGS. 5-8, the ear tube 200 comprises a first flange 216 and shaft 214 that may together comprise the first visual element 210, such as a first color or pattern. The second flange 218 may comprise the second visual element 212, such as a second color or pattern that is different than the first color or pattern. As the different shading indicates, the color combination and/or pattern combination in FIGS. 5-8 is different than the color combination and/or pattern combination in FIGS. 1-4. In another implementation, the ear tube 200 may comprise a third visual element, for example, a color band that is visually distinguishable from the first and second visual elements 210 and 212 disposed on the ear tube body 202.

Additionally, FIGS. 5-8 illustrate an implementation in which the material used to form the second flange 218 can be formulated with a reflective, retroreflective, or fluorescent additive to further enhance the visibility of the ear tube 200. The presence of reflective, retroreflective, or fluorescent additive can help identify the demarcation between the first visual element 210 and the second visual element 212. In this implementation, the first end 204 may comprise a visually distinguishable (e.g., unique) color and/or pattern. The second end 206 may comprise a different color and/or pattern than the first end 204. The color and/or pattern for the first end 204 may comprise a certain length of the ear tube 200 such that the surgeon positioning the ear tube 200 into the patient or observing an already placed ear tube 200 can have a visual indication if the ear tube 200 is in place.

Figure 9:
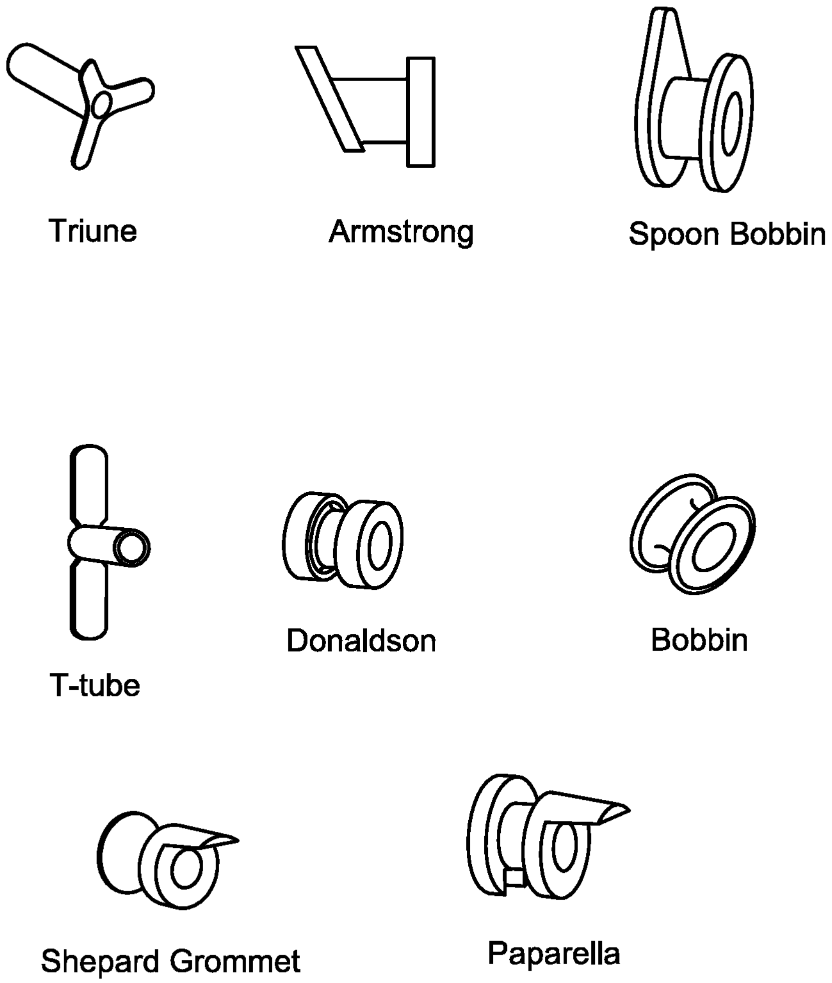
FIG. 9 is a set of diagrams illustrating different myringotomy tube shapes that are compatible with the disclosure provided herein.

Myringotomy tubes can be manufactured in different shapes, sizes, and from different materials. The most common materials may be silicone, fluoroplastic, and metal. As discussed above, a reflective, retroreflective, or fluorescent additive can be incorporated into the materials to increase visibility of the ear tube. The myringotomy tube may take any form chosen with sound engineering judgment, including a myringtomy tube, a T-tube, or a Triune tube. FIG. 9 illustrates different myringotomy tube shapes, including without limitation a T-shape, Triune tube, Armstrong tube, Spoon Bobbin tube, Donaldson tube, Bobbin tube, Shepard Grommet tube, and Paparella tube. Any ear tube shape can incorporate the visual elements (e.g., 110, 112 in FIGS. 1-4 and 210, 212 in FIGS. 5-8) of the present disclosure where one end of the ear tube is a different color and/or different pattern from the second end of the tube.

Figure 10:
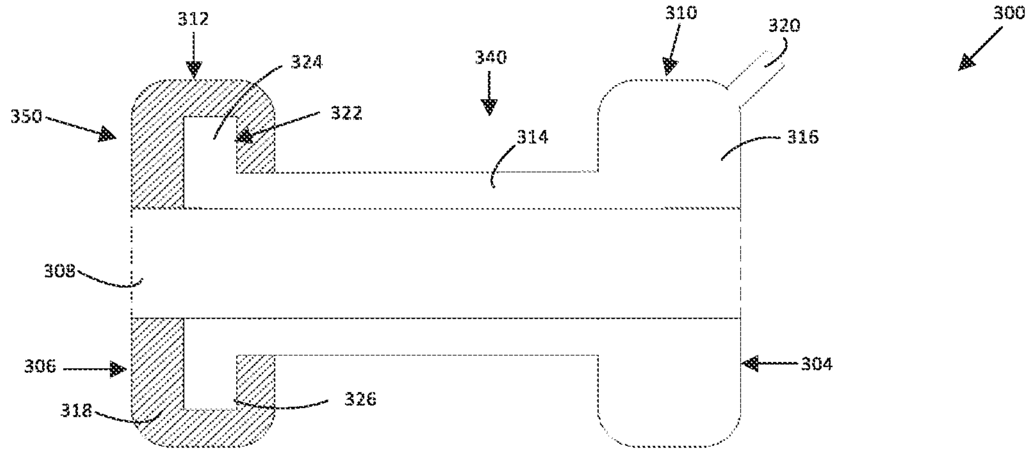
FIG. 10 is a cross sectional view of a myringotomy tube formed from multiple pieces of material according to one or more manufacturing techniques of this disclosure.

The ear tubes 100, 200 of FIGS. 1-8 can be manufactured from a single unitary structure or from multiple structures that are joined, or fused, together. Referring first to FIG. 10, there is an ear tube 300 comprising a first portion 340 and a second portion 350 that are fused together. The ear tube 300 may be fabricated by first forming a first portion 340 comprising a first visual element 310 from a molding process. The first portion 340 may comprise the first end 304, including the first flange 316 and tab 320 (e.g., if present), the shaft 314, and a retaining member 324. In this implementation, the first visual element 310 comprises a color and/or pattern that may be evenly distributed throughout the thickness of the body of the first portion 340.

The second portion 350 is formed over the first portion 340 through a molding process and comprises a second visual element 312. The second portion 350 may comprise a second end 306, including a second flange 318 and a receiving recess 326. In this implementation, the second visual element 312 comprises a color and/or pattern that may be evenly distributed throughout the thickness of the body of the second portion 350. After the second portion 350 has been molded over the first portion 340, there is a visually distinguishable line of demarcation defined by the first visual element 310 and the second visual element 312.

In some implementations, the ear tube 300 comprises a locking mechanism 322. The locking mechanism may comprise the retaining member 324 disposed on the first portion 340 at or near an end of the first portion 340 that is distal to the first end 304. In some implementations, the retaining member 324 can comprise a flange. In these implementations, the retaining member 324 is configured to be received in the receiving recess 326 formed in the second portion 350. The receiving recess 326 can have a size and shape that compliments the retaining member 324 to facilitate engagement between the retaining member 324 and receiving recess 326. In this manner, the locking mechanism 322 provides a mechanical impingement to mitigate, or perhaps even prevent, separation of the second portion 350 from the first portion 340. In other implementations, the retaining member 324 may comprise one or more arms that protrude outwardly from the body of the first portion 340 at or near the end of the first portion 340 that is distal to the first end 304. In those implementations, the protruding arms are configured to engage one or more receiving recesses formed in the second portion 350 to provide a mechanical impingement to mitigate, or perhaps even prevent, separation of the second portion 350 from the first portion 340.

In some implementations, the external surface of the retaining member 324 may be treated. For example, the surface of the retaining member 324 may be treated by manipulating or changing the external surface of the retaining member 324 (e.g., through texturing), to promote fusion between the first portion 340 and the second portion 350 when the second portion 350 is molded over the first portion 340. To enhance fusion between the first portion 340 and second portion 350, it can be beneficial for the first and second portions 340, 350 to be molded from the same or substantially the same materials such as, for example, silicone. Additionally, incorporating the locking mechanism 322 to act as a mechanical impingement can contribute to improved fusion and adhesion between the first portion 340 and second portion 350. In this manner, separation of the second portion 350 from the first portion 340 can be mitigated. The person of ordinary skill in the art will appreciate that separation of the second portion 350 from the first portion 340 can be a problem given the relatively small size of the ear tubes 300 (e.g., having a length less than 2 mm).

Figure 11:
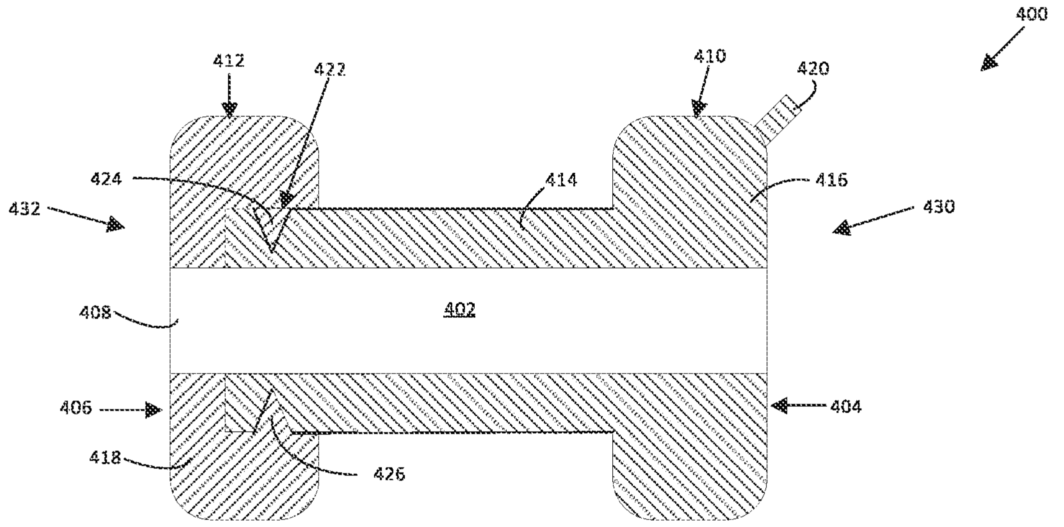
FIG. 11 is a cross sectional view of a myringotomy tube formed from multiple pieces of material according to one or more manufacturing techniques of this disclosure.

Referring now to FIG. 11, there is an ear tube 400 comprising a first portion 440 and a second portion 450 that are fused together much in the same manner as the ear tube 300 in FIG. 10. The primary difference between the ear tube 400 and the ear tube 300 is based on the structure of the locking mechanism 422.

The ear tube 400 may be fabricated by first forming a first portion 440 comprising a first visual element 410 from a molding process. The first portion 440 may comprise a first end 404, including a first flange 416 and a tab 420 (e.g., if present), a shaft 414, and a receiving recess 422. In this implementation, the first visual element 410 comprises a color, pattern and/or surface texture that may be evenly distributed throughout the thickness of the body of the first portion 440.

The second portion 450 may be formed over the first portion 440 through a molding process and may comprise a second visual element 412. The second portion 450 may comprise a second end 406, including a second flange 418 and a retaining member 426. In this implementation, the second visual element 412 comprises a color, pattern, and/or surface texture that may be evenly distributed throughout the thickness of the body of the second portion 450. After the second portion 450 has been molded over the first portion 440, there is a visually distinguishable line of demarcation established by the first visual element 410 and the second visual element 412.

In some implementations, the ear tube 400 comprises a locking mechanism 422. The locking mechanism 422 may comprise the receiving recess 424 disposed in the first portion 440 at or near an end of the first portion 440 that is distal to the first end 404. In some implementations, the receiving recess can have an annular structure. In these implementations, the receiving recess 424 is configured to receive the retaining member 426 disposed on the second portion 450. The receiving recess 426 can have a size and shape that compliments the retaining member 424 to facilitate engagement between the retaining member 424 and receiving recess 426. In this manner, the locking mechanism 422 provides a mechanical impingement to mitigate, or perhaps even prevent, separation of the second portion 450 from the first portion 440. In other implementations, the locking mechanism 422 may comprise one or more recesses disposed in the body of the first portion 440 at or near the end of the first portion 440 that is distal to the first end 404. In those implementations, the locking mechanism 422 comprises one or more recesses that are configured to receive one or more complimentary arms protruding form the second portion 450 to provide a mechanical impingement to mitigate, or perhaps even prevent, separation of the second portion 450 from the first portion 440.

In some implementations, the receiving recess 424 may be treated. For example, the surfaces defining the receiving recess 424 may be treated by manipulating or changing the surfaces defining the receiving recess 424 (e.g., through texturing), to promote fusion between the first portion 440 and the second portion 450 when the second portion 450 is molded over the first portion 340. To enhance fusion between the first portion 440 and second portion 450, it can be beneficial for the first and second portions 440, 450 to be molded from the same or substantially the same materials such as, for example, silicone. Additionally, incorporating the locking mechanism 422 to act as a mechanical impingement can contribute to improved fusion and adhesion between the first portion 440 and second portion 450. In this manner, separation of the second portion 450 from the first portion 440 can be mitigated. The person of ordinary skill in the art will appreciate that separation of the second portion 450 from the first portion 440 is a problem given the relatively small size of the ear tubes 400 (e.g., having a length less than 2 mm).

Figure 12:
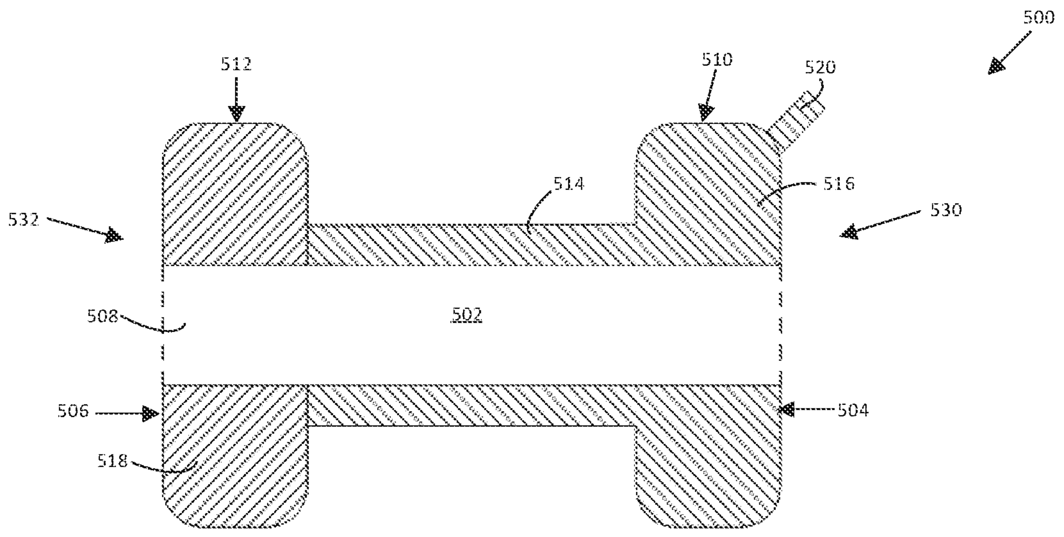
FIG. 12 is a cross sectional view of a myringotomy tube formed from one piece of material according to one or more manufacturing techniques of this disclosure

Referring now to FIG. 12, there is an ear tube 500 comprising a single unitary tube body 502. In this implementation, silicone material can be injected in precise quantities at one time into a mold from two different locations that are disposed laterally 530, 532 relative to fabricated ear tube 500. It should be understood that any material chosen with sound engineering judgment may be utilized to achieve the desired visual element. The silicone material injected at location (e.g., a first injection port) can comprise a first color and/or pattern that is configured to act as a first visual element 510. The silicone material injected at the other location 532 (e.g., a second injection port) can comprise a second color and/or pattern that is configured to act as a second visual element 512. The first color and/or pattern is visually distinguishable from the second color and/or pattern. During the fabrication process, the silicone materials injected from the two locations 530 and 532 meet resulting in the formation of a clear line of demarcation between the first visual element 510 and the second visual element 512 due to the first color and/or pattern being visually distinguishable from the second color and/or pattern. After the molding process, the the first color and/or pattern may be evenly distributed throughout a first portion of the tube body 502 and the second color and/or pattern may be evenly distributed throughout a second portion of the tube body 502.

Figure 14:
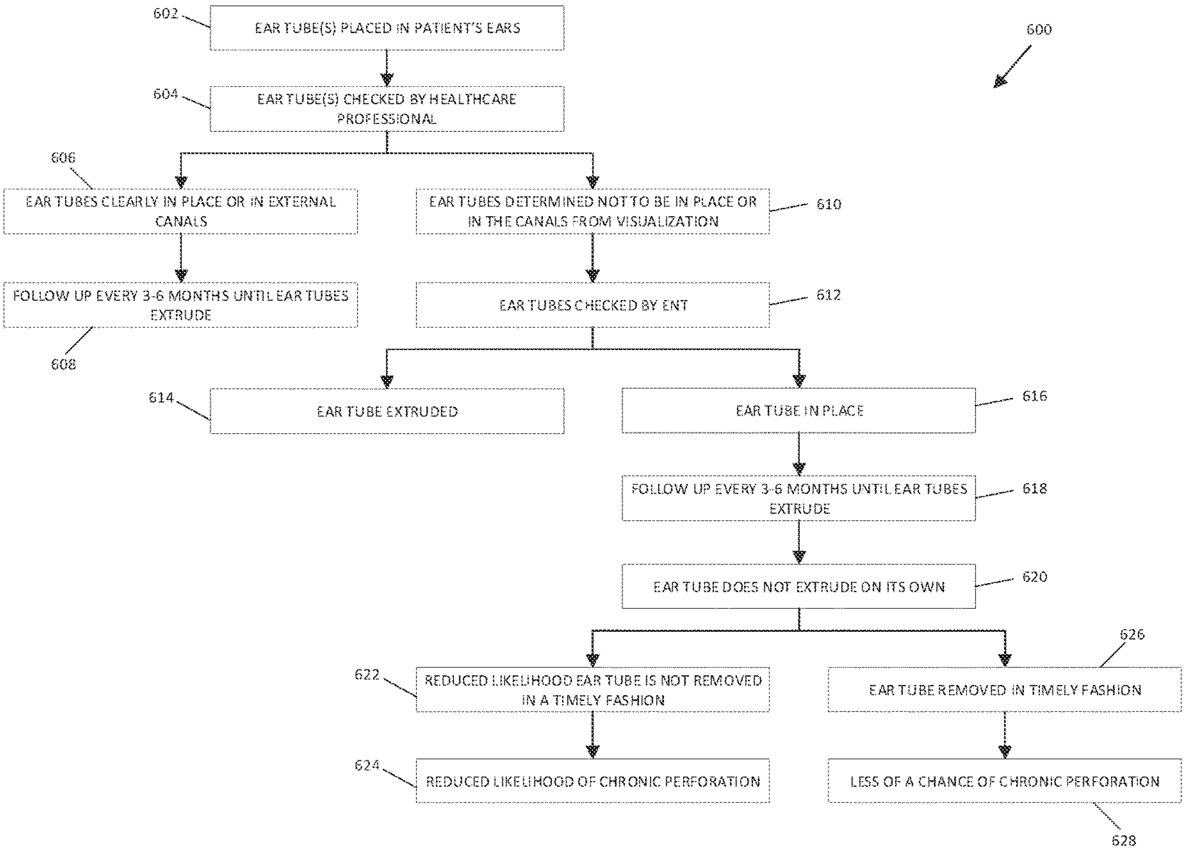
FIG. 14 is a flow diagram providing an example implementation for using the myringotomy tubes of this disclosure.

Referring now to FIG. 14, there is a flow diagram illustrating an example implementation 600 of using an ear tube of this disclosure, or myringotomy tube, that comprises one or more visual elements. At 602, the ear tubes are placed in a patient's ears by a medical professional to treat recurrent or chronic otitis media. During insertion of the ear tube 100, the surgeon is provided with a multi-colored ear tube 100 as described. One end of the tube is inserted into the patient's ear drum or tympanic membrane until the first visual element, such as the first color is no longer visible and only the second visual element, or second color is visible. The visual indication provides a simple verification of proper placement of the ear tube. The visual element demarcation such as color, pattern, or surface texture demarcation, also provides for easy checks over time to determine if the ear tube is still in its proper position.

At 604, the ear tubes are checked by a healthcare professional such as, for example, a pediatrician, internists, family practice, nurse practitioner, etc. At 606, the ear tubes are determined to be clearly in place or clearly in external canals of the patient. At 608, upon this determination, there is a follow-up appointment scheduled every 3-6 months until the ear tubes extrude.

At 610, it is unclear whether the tubes are in place or in the canals of the patient. Advantageously, the ear tubes of this disclosure are easier to visualize and to determine if the ear tubes are in place. Therefore, the ear tubes of the present disclosure beneficially result in fewer referrals to the ENT.

At 612, there is an instance of referring a patient to an ENT specialist to check the tubes. At 614, the ENT determines the ear tubes are extruded. At 616, the ENT determines the ear tube is in place. At 618, upon this determination, there is a follow-up appointment scheduled every 3-6 months until the ear tubes extrude. At 620, is a scenario in which the ear tube does not extrude on its own. As indicated at 622, there is a reduced likelihood that an ear tube of this disclosure is not removed in a timely fashion. This is because the ear tubes provided herein are easier to visually assess if they are still in place in the patient's ear. At 624, there is a reduced likelihood of chronic perforation. At 626, the ear tube is removed in a timely fashion. At 628, there is less of a chance of chronic perforation as a result of removing the tube in a timely fashion, which can be done with greater accuracy given the helpful indicia provided by the visual elements.

The word "exemplary" is used herein to mean serving as an example, instance or illustration. Any aspect or design described herein as "exemplary" is not necessarily to be construed as advantageous over other aspects or designs. Rather, use of the word exemplary is intended to present concepts in a concrete fashion. As used in this application, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Further, at least one of A and B and/or the like generally means A or B or both A and B. In addition, the articles "a" and "an" as used in this application and the appended claims may generally be construed to mean "one or more" unless specified otherwise or clear from context to be directed to a singular form.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims. Of course, those skilled in the art will recognize many modifications may be made to this configuration without departing from the scope or spirit of the claimed subject matter.

Also, although the disclosure has been shown and described with respect to one or more implementations, equivalent alterations and modifications will occur to others skilled in the art based upon a reading and understanding of this specification and the annexed drawings. The disclosure includes all such modifications and alterations and is limited only by the scope of the following claims. In particular regard to the various functions performed by the above described components (e.g., elements, resources, etc.), the terms used to describe such components are intended to correspond, unless otherwise indicated, to any component which performs the specified function of the described component (e.g., that is functionally equivalent), even though not structurally equivalent to the disclosed structure which performs the function in the herein illustrated exemplary implementations of the disclosure.

In addition, while a particular feature of the disclosure may have been disclosed with respect to only one of several implementations, such feature may be combined with one or more other features of the other implementations as may be desired and advantageous for any given or particular application. Furthermore, to the extent that the terms "includes," "having," "has," "with," or variants thereof are used in either the detailed description or the claims, such terms are intended to be inclusive in a manner similar to the term "comprising."

The implementations have been described, hereinabove. It will be apparent to those skilled in the art that the above methods and apparatuses may incorporate changes and modifications without departing from the general scope of this invention. It is intended to include all such modifications and alterations in so far as they come within the scope of the appended claims or the equivalents thereof.

What is claimed is:

1. An ear tube, comprising:

a tube body comprising a first, distal end, a second, proximal end, and a shaft operably connecting the first, distal end and the second, proximal end, the ear tube having a total length L that extends between the first, distal end and the second, proximal end, wherein the tube body is a single unitary piece comprising a first material;

wherein the first, distal end comprises a first visual element, the first visual element is a first color;

wherein the second, proximal end comprises a second visual element, the second visual element is a second color different than the first color;

wherein the first visual element is different than the second visual element such that the first visual element is visually distinguishable from the second visual element;

wherein the ear tube comprises a visually distinguishable line of demarcation between the first visual element and the second visual element, the first and second visual elements configured to visually indicate whether the ear tube is present in a patient's tympanic membrane such that when the ear tube is present in the patient's tympanic membrane, the first, distal end is inserted in the patient's tympanic membrane and not visible while the second, proximal end is visible; and wherein the first and second visual elements are part of the single unitary piece of the tube body, the first visual element comprising the first material and a first pigment and the second visual element comprising the first material and a second pigment different than the first pigment.

2. The ear tube of claim 1, wherein the first, distal end comprises a first flange and the second, proximal end comprises a second flange, and the shaft interconnects the first flange and the second flange, wherein a lumen extends through each of the first flange, the shaft, and the second flange, the first visual element being disposed on the first flange and the shaft, and the second visual element being disposed on the second flange.

3. The ear tube of claim 2, wherein the tube body further comprises a third visual element.

4. The ear tube of claim 3, wherein the third visual element is a color band that is visually distinguishable from the first visual element and the second visual element.

5. The ear tube of claim 2, wherein the second visual element on the second flange further comprises a reflective, retroreflective, or fluorescent additive to further enhance visibility of the ear tube.

6. The ear tube of claim 1, wherein the total length L of the ear tube is less than 2 mm.

7. The ear tube of claim 1, wherein the first color of the first visual element is visually distinguishable from the second color of the second visual element and forms the visually distinguishable line of demarcation between the first visual element and the second visual element, wherein the first visual element and the second visual element comprise one or more of the following color combinations: Blue-Green; Blue-Yellow; Blue-Red; Blue-Violet; White-Black; White-Blue; White-Green; White-Red; White-Yellow; White-Violet; Black-Blue; Black-Green; Black-Red; Black- Violet; Black-Yellow; Green-Red; Green-Yellow; Green-Violet; Yellow-Red; and Yellow-Violet.

8. The ear tube of claim 1, wherein the tube body comprises one or more of a T-shape, Triune tube, Armstrong tube, Spoon Bobbin tube, Donaldson tube, Bobbin tube, Shepard Grommet tube, and Paparella tube.

9. The ear tube of claim 1, wherein the first material of the first visual element and the second visual element is silicone.

10. The ear tube of claim 1, wherein the first visual element has a length that extends a portion of the total length L of the ear tube, and the length of the first visual element is configured to serve as a visual indicator to assist with placement of the ear tube in the patient's tympanic membrane.

11. An ear tube, comprising:

a tube body comprising a first, distal end, a second, proximal end, and a shaft operably connecting the first, distal end and the second, proximal end, the ear tube having a total length L that extends between the first, distal end and the second, proximal end, wherein the tube body is a single unitary piece comprising a first material;

wherein the first, distal end comprises a first visual element, the first visual element is a first color;

wherein the second, proximal end comprises a second visual element, the second visual element is a second color different than the first color;

wherein the first visual element is different than the second visual element such that the first visual element is visually distinguishable from the second visual element;

wherein the first visual element and the second visual element are part of the single unitary piece of the tube body, the first visual element comprising the first material and a first pigment and the second visual element comprising the first material and a second pigment such that the first and second visual elements are formed from the same first material;

wherein the first pigment is different than the second pigment; and wherein the ear tube comprises a visually distinguishable line of demarcation between the first visual element and the second visual element, the first and second visual elements configured to visually indicate whether the ear tube is present in a patient's tympanic membrane such that when the ear tube is present in the patient's tympanic membrane, the first, distal end is inserted in the patient's tympanic membrane and not visible while the second, proximal end is visible.

12. The ear tube of claim 11, wherein the first, distal end comprises a first flange and the second, proximal end comprises a second flange, and the shaft interconnects the first flange and the second flange, wherein a lumen extends through each of the first flange, the shaft, and the second flange, the first visual element being disposed on the first flange and the shaft, and the second visual element being disposed on the second flange.

13. The ear tube of claim 12, wherein the tube body further comprises a third visual element, wherein the third visual element is visually distinguishable from the first visual element and the second visual element, and optionally, the third visual element is a color band.

14. The ear tube of claim 12, wherein the second visual element on the second flange further comprises a reflective, retroreflective, or fluorescent additive to further enhance visibility of the ear tube.

15. The ear tube of claim 11, wherein the total length L of the ear tube is less than 2 mm.

16. The ear tube of claim 11, wherein the first color of the first visual element is visually distinguishable from the second color of the second visual element and forms the visually distinguishable line of demarcation between the first visual element and the second visual element, wherein the first visual element and the second visual element comprise one or more of the following color combinations: Blue-Green; Blue-Yellow; Blue-Red; Blue-Violet; White-Black; White-Blue; White-Green; White-Red; White-Yellow; White-Violet; Black-Blue; Black-Green; Black-Red; Black-Violet; Black-Yellow; Green-Red; Green-Yellow; Green-Violet; Yellow-Red; and Yellow-Violet.

17. The ear tube of claim 11, wherein the first material comprises silicone.

18. The ear tube of claim 11, wherein the first visual element has a length that extends a portion of the total length L of the ear tube, and the length of the first visual element is configured to serve as a visual indicator to assist with placement of the ear tube in the patient's tympanic membrane.

* * * * *